United States Patent
Nguyen

(10) Patent No.: US 7,180,980 B2
(45) Date of Patent: Feb. 20, 2007

(54) METHOD FOR INTENSITY MODULATED RADIATION TREATMENT USING INDEPENDENT COLLIMATOR JAWS

(75) Inventor: John Nguyen, Danville, CA (US)

(73) Assignee: Prowess, Inc., Chico, CA (US)

( * ) Notice: Subject to any disclaimer, the term of this patent is extended or adjusted under 35 U.S.C. 154(b) by 63 days.

(21) Appl. No.: 10/924,774

(22) Filed: Aug. 25, 2004

(65) Prior Publication Data

US 2006/0045238 A1    Mar. 2, 2006

(51) Int. Cl.
*A61N 5/10*    (2006.01)

(52) U.S. Cl. .................. 378/65; 378/148; 378/149; 378/151

(58) Field of Classification Search .............. 378/64, 378/65, 147–153
See application file for complete search history.

(56) References Cited

U.S. PATENT DOCUMENTS 5,748,703 A * 5/1998 Cosman ................. 378/152
5,818,902 A   10/1998 Yu
6,473,490 B1  10/2002 Soichi
2004/0071261 A1 * 4/2004 Earl et al. ................. 378/65

OTHER PUBLICATIONS

Webb, Steve. Intensity-modulated radiation therapy using only jaws and a mask: II. A simplified concept of relocatable single-bixel attenuators. Physics in Medicine and Biology, Institute of Physics Publishing. Phys. Med. Biol. 47, pp. 1869-1879 (2002).

* cited by examiner

Primary Examiner—Edward J. Glick
Assistant Examiner—Jurie Yun
(74) Attorney, Agent, or Firm—Connolly Bove Lodge & Hutz LLP; Myron Keith Wyche

(57) ABSTRACT

The present invention is a method for treatment planning and delivery of the radiation treatment plan for the intensity-modulated radiation therapy (IMRT) treatment using linear accelerators (LINACs) not equipped with a multileaf collimator (MLC). The present invention makes the use of a simpler collimator consisting of only 4 collimator jaws. In addition, the method for treatment planning of the present invention may be performed on a computer separate from the LINAC control computer, so that the treatment planning system can generate IMRT treatment plans for LINACs and collimator jaws from different vendors.

14 Claims, 4 Drawing Sheets

US 7,180,980 B2

METHOD FOR INTENSITY MODULATED RADIATION TREATMENT USING INDEPENDENT COLLIMATOR JAWS

BACKGROUND OF THE INVENTION

The present invention relates to a computerized method for the planning and delivery of radiation therapy. In particular, it is a computerized method that determines the optimal radiation treatment plan for a patient using specified clinical objectives.

In general, radiation therapy is the use of ionizing radiation for the treatment of disease. The most common use is in the treatment of cancer. The goal of radiation therapy in cancer treatment is to destroy any malignant cells while minimizing the damage to healthy tissue. One example of a device for delivering the radiation to a patient is a linear accelerator (LINAC). A LINAC is a machine that generates a high-energy beam of radiation that can be controlled and directed onto specified locations. LINACs are sometimes equipped with a multi-leaf collimator (MLC). A MLC is a device that shapes each individual beam of radiation. Alternatively, a LINAC may not be equipped with a MLC, but instead use four collimation jaws that can be individually controlled to shape a rectangular radiation field.

FIG. 1 is an exemplary diagram of a background art radiation therapy system 2. The radiation therapy system of FIG. 1 shows the external structure of a LINAC with a rotating gantry 6 mounted on a stationary stand 9. A LINAC waveguide (not shown in FIG. 1, but normally located inside the gantry 6) accelerates the electrons to produce high energy radiation beams. The gantry 6 swivels the LINAC on a horizontal axis of rotation 8 around the patient 13 who is lying on a bed 16. The LINAC is a device capable of controlled delivery of radiation to target 12 in the body of the patient 13 being treated by the radiation therapy system 2. The radiation exits through the end of the treatment head 4 that is mounted on the gantry 6. In some LINACs, the treatment head is equipped with a MLC (not shown in FIG. 1, but normally located inside the treatment head 3) that can shape the radiation fields that exit the treatment head 4 into arbitrary shapes. In some radiation therapy systems 2, the treatment head 4 is equipped with simpler collimator jaws (not shown in FIG. 1, but normally located inside the treatment head 4) instead of a MLC. In most cases, each collimator jaw can move independently to shape a rectangular field. In addition, the radiation therapy system 2 has a control unit 200 in a housing 18 at least one display unit 70 and a keyboard 19.

During treatment, the LINAC emits a beam of radiation 10 is aimed at the target 12 in the body of the patient 13. As a non-limiting example, the beam of radiation can be photons, electrons, or any other type of radiation used in background art radiation therapy systems. The gantry 6 can rotate about a horizontal axis of rotation 8 around the patient 13 and thus allows for a change in the angle of the beam of radiation 10.

FIG. 2 is an exemplary diagram of a background art MLC 401. The MLC 401 is shown in FIG. 2 is a beam shielding device that is provided within the treatment head 4 (FIG. 1) and is in the path of beam of radiation 10. The MLC 401 beam shielding device determines the irradiated field that impinges the target 12 in the body of the patient 13 (FIG. 1). As shown in FIG. 2, the MLC 401 may include a plurality of leaves 41a, 41b . . . 41n, 42a, 42b . . . 42n, though only one pair 41a, 42a is discussed for convenience. In addition, as shown in FIG. 2, a plurality of drive units 43a, 43b . . . 43n, 47a, 47b . . . 47n, is used to position the plurality of leaves 41a, 41b . . . 41n, 42a, 42b . . . 42n, though only one pair 43a, 47a is discussed for convenience. Moreover, additional pairs of leaves (not shown) may be arranged perpendicular to the plurality of leaves 41a, 41b . . . 41n, 42a, 42b . . . 42n. It is to be understood that the discussion is applicable to the plurality of leaves and the plurality of drive units.

The leaves 41a, 42a are moved by a drive unit 43 in order to change the size of the irradiated field. The drive units 43a, 47a may further include, for example, an electric motor (not shown) that is coupled to the leaves 41a and 42a and is controlled by a motor controller (not shown) that is provided by the control unit 200 (FIG. 1). In addition, position sensors (not shown) may also be coupled to the leaves 41a and 42a, respectively. The MLC 401 arrangement includes the plurality of leaves 41a, 41b . . . 41n, 42a, 42b . . . 42n for blocking radiation and can approximate shapes other than a rectangle. The plurality of leaves 41a, 41b . . . 41n, 42a, 42b, . . . 42n are relatively narrow and cast a shadow of about 0.5 to 1.0 cm in width onto the target 12 (FIG. 1). The more leaves that are used, the more complicated the MLC 401 becomes.

Treatment planning for conventional cancer radiation treatment is often performed with the aid of three-dimensional images of the patient acquired by using a computed tomography (CT) scanner. Based on these images, a radiation oncologist can pinpoint the location of a target tumor and any surrounding sensitive structures. Based on this information, a treatment planner (e.g., a dosimetrist) devises the configuration of radiation beams that will deliver the desired radiation dose to the patient. The parameters that need to be determined by the dosimetrist include: (1) beam energies, (2) beam orientations and (3) field shapes.

Conventionally, using a trial-and-error approach, the dosimetrist determines an acceptable configuration of the various parameters that meets the clinical goals specified by the radiation oncologist. In this technique, referred to as "forward-planning," the dosimetrist and the radiation oncologist devise the configuration of radiation beams, the computer control unit proceeds according to their direction. If the dosimetrist and radiation oncologist are not satisfied with the radiation dose distribution, they will redefine alternative beam energies, beam orientations and field shapes until a satisfactory result is produced. Therefore, in "forward-planning" approach, human being determines the parameters that produce the best treatment plan.

While background art treatment planning using the "forward-planning" technique for conventional cancer radiation treatment has achieved some success, shaping the radiation field alone provides limited freedom in shaping the volume of the high radiation dose to conform to the tumor. As a result, adverse effects can arise in the patient being treated because of irradiation of normal structures in the "forward-planning" technique to treatment planning.

A recent development in radiation therapy is intensity-modulated radiotherapy (IMRT). In IMRT, the intensity of the radiation is modulated within each field delivered. The purpose of IMRT is to sculpt the radiation dose distribution in order to maximize the radiation dose to the cancerous tumor while limiting the radiation dose to normal structures within some pre-specified tolerance. In IMRT, highly conformal dose distributions can be achieved through the delivery of optimized non-uniform radiation beam intensities from each beam angle. Successful delivery of IMRT can allow for an escalation of the radiation dose to the target tumor that can enhance local tumor control. These dosimetric advantages of IMRT can also be used to provide a reduced probability of complications due to adverse effects due to radiation exposure on normal tissue.

Due to the complexity of treatment plans for IMRT, a computer is used to determine radiation intensity maps that produce an optimal radiation dose distribution. In contrast to the "forward planning" techniques of the background art that use a human to determine the parameters, this approach is termed "inverse-planning" because the computer determines the parameters that produce the optimal radiation treatment plan.

For IMRT treatment delivery, the desired radiation intensity map derived by the computer is converted into overlapping field shapes, called sub-fields or field segments. By delivering these field segments along the same beam angle, the patient receives the desired intensity distribution. This series of beam shapes are delivered either dynamically or in a step-and-shoot fashion.

In most background art intensity-modulated delivery techniques, it is necessary that the LINAC be equipped with a MLC. As shown in FIG. 2, the MLC is a complicated device that is generally made of a plurality of tungsten leaves driven by a plurality of drive units equipped with motors. The cost of a MLC is a substantial portion of the cost of the radiation delivery device (i.e., the LINAC).

However, as discussed above, not all LINACs are equipped with a MLC due to the substantial cost involved. In fact, older LINACs currently in use are not equipped with a MLC but only with collimator jaws. In the case of a LINAC without a MLC, radiation field shaping is achieved with just the collimator jaws. The collimator jaws are two pairs of tungsten blocks. In most cases, at least one pair of jaws can move independent of the other to form fields that are asymmetric with respect to the central axis of the beam. This type of radiation blocking device is often referred to as "independent jaws."

A limitation of these independent collimator jaws is that these radiation blocking devices can only form rectangular fields. Due to this limitation, the delivery of IMRT using collimator jaws alone was thought to be impractical. In a paper entitled "Intensity-modulated radiation therapy using only jaws and a mask," by Webb, a technique that places a relocatable mask below the collimator jaws was proposed as a practical approach for the delivery of IMRT treatments. However, use of such a relocatable mask introduces different practical issues and adds cost. Thus, to date there is no known treatment planning system for planning IMRT treatments using collimator jaws alone that does not include practical implementation problems and increased costs.

Due to the reasons stated above, background art IMRT treatment planning systems typically rely on the use of MLCs. These background art techniques are typically performed in two steps: (1) optimizing the radiation intensity maps; and (2) converting the radiation intensity maps to deliverable field segments. However, these background art techniques for IMRT treatment planning typically perform the optimizing step without consideration of the delivery constraints of either the MLC or the LINAC.

Non-limiting examples of the delivery constraints of the MLC include: the speed of leaf travel; the ability to close the opposing leaves; and the ability to slide the opposing leaves across each other. Non-limiting examples of the delivery constraints on the LINAC include the dose rate and the minimal amount of radiation that can be delivered with acceptable accuracy. Ignoring these delivery constraints of the LINAC and MLC in the optimizing step of the treatment plan makes the second step of converting from the intensity maps to deliverable field segments more complex. As a result of this increased complexity, a large number of field segments are required to produce the desired radiation intensity distribution.

In addition, background art IMRT treatment planning techniques rely on the division of the radiation field segments into beamlets. The size of these beamlets is typically 1 cm×1 cm. In the background art, the radiation intensities (i.e., weighting) of the beamlets are typically determined by either turning-on or turning-off beamlets. Thus, the boundary of the resultant radiation beam used to treat a target tumor is constrained to some multiple of the size of the beamlets (e.g., 1 cm×1 cm). For example, a spherical tumor with a 2 cm diameter can only be treated with a square radiation field of beamlets with 2 cm sides (i.e., a square field composed of four 1 cm×1 cm beamlets). If such small tumors are very close to a critical healthy tissue structure, the square radiation field of beamlets will cover both the target tumor and adjacent healthy tissue structures. Therefore, as a result of the size of the beamlets, the shape of the square radiation field segment fails to conform to the shape of the target tumor.

Further, the use of beamlets in background art treatment planning systems also fixes the orientation of the collimator to the orientations of the grid lines. Since the target tumor can be viewed from different beam angles in the beam's eye view (BEV), a fixed collimator would not allow the MLC to best conform to the shape of the tumor. This limitation of the MLC further increases the complexity of delivery constraints that should be considered in treatment planning systems.

In summary, the key techniques in the radiation therapy systems of the background art include the two-step approach of: (1) obtaining the intensity maps; and (2) converting the intensity maps into deliverable field segments. In addition, the division of the beam portal defines the radiation beam's BEV for each radiation beam angle into a set of finite-sized beamlets. As discussed above, each of the background art techniques has certain practical limitations. Further, the use of collimator jaws alone further constrains the shape of the radiation field segments to rectangles. These finite-sized rectangular field shapes may require hundreds of rectangular fields to achieve a desired dose distribution. Such a large number of rectangular fields would require hours of time to deliver and would clearly be impractical.

Therefore, there is a need in the art for more practical, cost efficient and time effective methods of inverse-planning treatment for IMRT. In particular, there is a need for a method for using independent collimator jaws alone that overcomes the limitations of the background art.

SUMMARY OF THE INVENTION

The present invention is a method for treatment planning and delivery of the radiation treatment plan for the IMRT technique. Specifically, while background art treatment planning systems for IMRT generally require the use of a MLC, the present invention makes use of a simpler independent collimator consisting of only 4 collimator jaws. In addition, the method for treatment planning of the present invention is performed on a computer separate from the LINAC control computer, so that the planning system can generate IMRT treatment plans for LINACs and collimator jaws from different vendors.

As discussed above, the present invention is an inverse-planning method that does not require the radiation therapy system to be equipped with a MLC. In particular, to make the delivery of IMRT using collimator jaws alone practical, the present invention abandons the background art concept of beamlets. That is, instead of performing the two step approach used in the background art of: (1) optimizing the intensities of the beamlets; and (2) translating the radiation intensity map into field shapes; the present invention instead directly optimizes the field shapes and their weightings. Since there is no finite-sized beamlet grid that puts constraints on the orientation of the apertures, each of the rectangular sub-fields, or segments, can take a different collimator angle.

The combination of directly optimizing the shapes and weights of the field segments and the freedom of allowing the apertures to take different orientations provides added freedom in the treatment planning problem. The present invention uses this added freedom to compensate for the limitations posed by background art radiation therapy systems with collimator jaws only that form rectangular radiation field segments. In particular, the method of the present invention makes it possible to generate IMRT treatment plans with radiation field segments that a highly conformal to the target tumor without using impractically large numbers of radiation field segments, as required by the background art.

One embodiment of the invention is a method for optimizing radiation therapy that directly optimizes deliverable rectangular fields that overlap at each beam angle and creates intensity modulations for radiation treatment systems, said method comprising: selecting a number of delivery angles, wherein each of the delivery angles has at least one aperture; assigning initial collimator angles to each of the apertures; assigning initial aperture shapes for each of the plurality of discrete pencil beam delivery angles; defining geometric constraints for a delivery mode and a LINAC; selecting clinical objectives; calculating the dose contribution of each of a plurality of discrete pencil beams; calculating dose distribution and the value of the objective function for each delivery angle; altering at least one of the collimator angles, aperture shapes and weights based on a predetermined selection procedure when any of the constraints for the delivery mode are violated; calculating dose distribution resulting from altering at least one of the collimator angles, aperture shapes and weights based on the predetermined selection procedure; determining whether the constraints on delivery and the clinical objectives of the radiation therapy are met; calculating the objective functions based on the dose distribution; determining whether to at least one of accept or reject a change in parameters based on at least one optimization method; outputting resulting aperture shapes, weights and dose distribution for optimized radiation therapy when the change in parameters is accepted.

DETAILED DESCRIPTION OF THE INVENTION

The present invention enables IMRT treatments to be delivered with the use of simple independent collimator jaws. Instead of optimizing the intensities of beamlets, the present invention directly optimizes the field shapes and the corresponding weights of the rectangular apertures formed by the simple independent collimator jaws. Furthermore, the optimization step of the present invention does not explicitly use beamlets and thus allows the simple independent collimator jaws to form field boundaries at any position (i.e., not merely at increments of a finite-sized beamlet). The method of the present invention allows each rectangular field shaped by the collimator jaws to take a different collimator angle. The combination of these optimally weighted apertures with optimal collimator angles at every beam angle creates a highly modulated radiation intensity distribution for achieving the clinical objectives of the treatment plan. Since the field boundaries are not limited by the size of the beamlets, the quality of the treatment plans using the collimator jaws can rival those using a MLC and planning methods of the background art without adding much extra burden on the treatment delivery.

Figure 3:
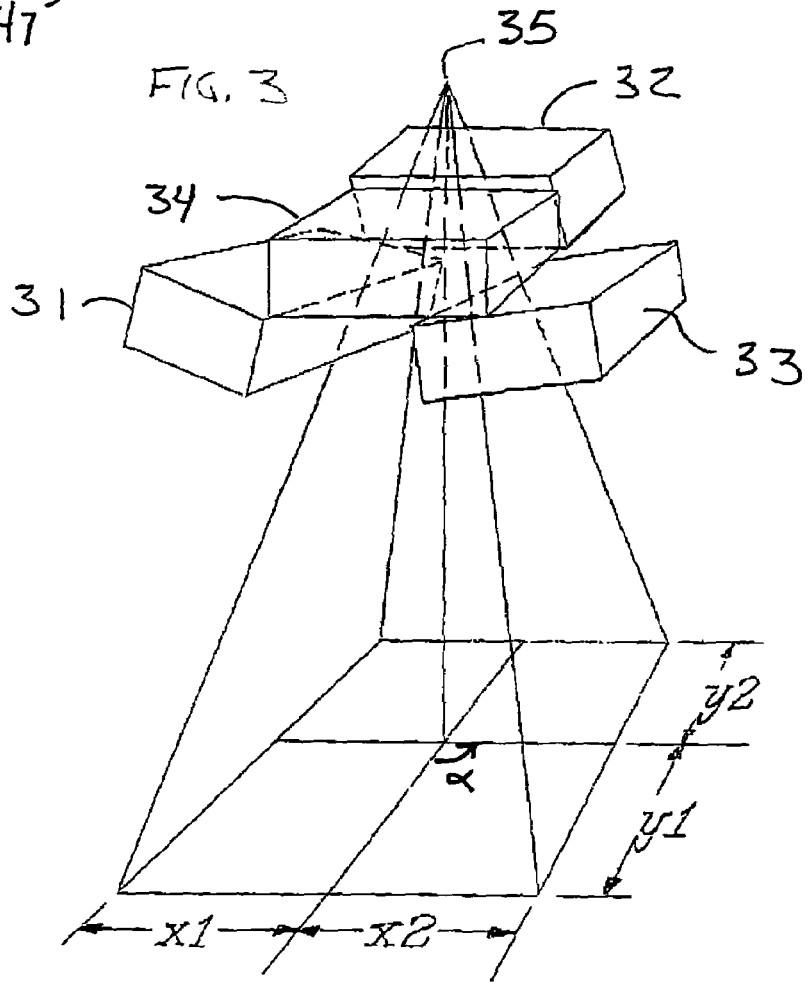
FIG. 3 is an exemplary diagram of a simple independent collimator jaws of the present invention.

FIG. 3 is an exemplary diagram of the simple independent collimator jaws of the present invention. The two lower jaws 31, 33 determine the positions of the x-axis coordinates x1, x2, respectively, and the two upper jaws 32, 34 determine the positions of the y-axis coordinates y1, y2, respectively, of the beam aperture.

Figure 1:
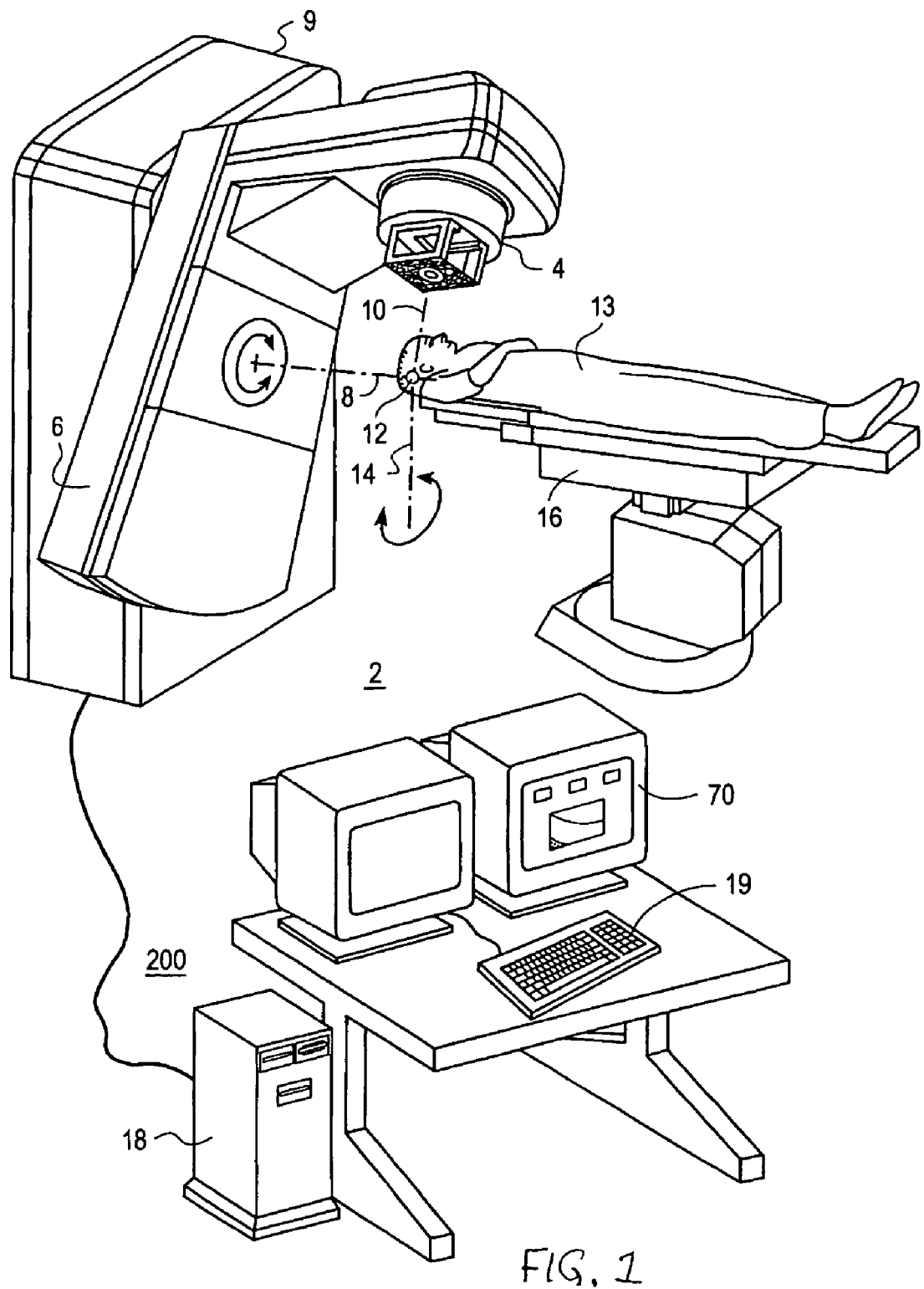
FIG. 1 is an exemplary diagram of a background art radiation therapy system.
Figure 4:
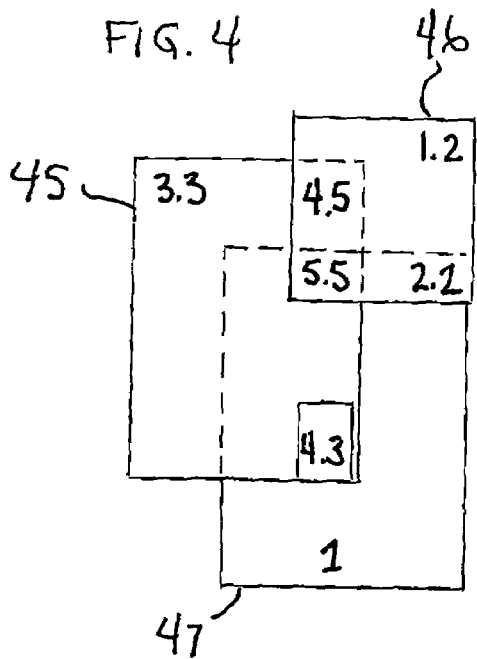
FIG. 4 illustrates an example intensity distribution for 3 rectangular aperture shapes as determined by the present invention that shows the highly modulated beam intensities that results from their overlap.
Figure 5:
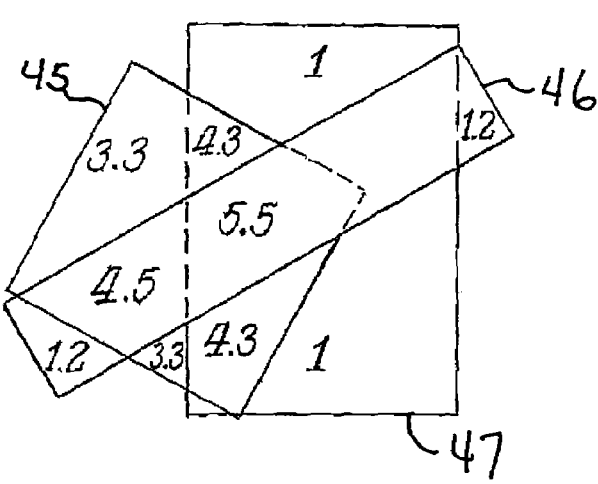
FIG. 5 illustrates another example intensity distribution resulting from 3 rectangular aperture shapes of different orientations as determined by the present invention that shows the highly modulated beam intensities that results from their overlap.

As shown in FIG. 3, the simple independent collimator jaws is a radiation beam 35 shielding device that has four jaws arranged as two lower jaws 31, 33 and two upper jaws 32, 34. In a non-limiting example, these jaws 31, 32, 33, 34 are made of tungsten alloy or other heavy metal materials. Each jaw can generally move independently of the others. As a result, rectangular field shapes can be formed at different sizes and locations, as shown in FIG. 4 and FIG. 5 that are discussed below. The entire treatment head (FIG. 1, reference 4) can rotate around the axis of the radiation beam 35. The angle of rotation $\alpha$ is referred to as the collimator angle. Thus, the orientation of the rectangular beam aperture field shapes formed by the independent collimator jaws 31, 32, 33, 34 can take on different angles. The range of movement of the jaws 31, 32, 33, 34 varies among different radiation therapy systems (FIG. 1, reference 2) and such constraints can be entered into the treatment planning system so that no unrealizable rectangular radiation field shapes are generated.

The intensity (i.e., weight) of a beam refers to the amount of radiation that is generated at a specific location of the treatment portal by the LINAC. A longer radiation exposure time at a specific spot in the treatment portal corresponds to larger radiation intensity. If the collimator jaws opening is fixed during the entire duration of the radiation treatment, all points in the treatment portal would receive approximately the same amount of radiation, and there would be no intensity modulation. However, an IMRT radiation field is seen if the treatment portal consists of multiple field segments, each of which lets different amounts of radiation pass to the patient and each of which overlaps partially with other field segments. As a result, some portions of the treatment portal are exposed for a longer time and have larger radiation intensity than other portions of the treatment portal.

FIG. 4 illustrates an example intensity distribution for 3 rectangular beam aperture shapes 45, 46, 47 of the present invention when the collimator angle α=0. FIG. 3 shows that a range of highly modulated beam intensities results from the overlap of the beam aperture shapes 45, 46, 47. In particular, rectangular beam aperture 45 has a weight of 3.3, rectangular beam aperture 46 has a weight of 1.2 and rectangular beam aperture 47 has a weight of 1. However, as a result of the overlap of the individual rectangular beam apertures 45, 46, 47, additional weights of 2.2, 4.3, 4.5 and 5.5 are also provided by the various combinations of the three individual apertures 45, 46, 47.

Alternatively, as a non-limiting example of the rectangular shapes of FIG. 4, the collimator angle α may be varied such that each rectangular beam aperture starts with different orientations. This may act to further ease the optimization process to be discussed below. FIG. 5 illustrates an example of such an intensity distribution for 3 rectangular beam aperture shapes as determined by the present invention. As in FIG. 4, rectangular beam aperture 45 has a weight of 3.3, rectangular beam aperture 46 has a weight of 1.2 and rectangular beam aperture 47 has a weight of 1. However, as a result of the overlap of the individual rectangular beam apertures 45, 46, 47, additional weights of 2.2, 4.3, 4.5 and 5.5 are also possible from various combinations of the three rectangular beam apertures 45, 46, 47. As a result of the different collimator angles α, the intensities (i.e., weights) can be placed in a wider variety of positions in the x-y coordinate plane of the radiation field. Thus, the method of the present invention with more freedom in delivering the appropriate radiation dose to the position of the target tumor and a greater ability to avoid healthy tissues.

FIG. 4 and FIG. 5 illustrates the intensity distribution created with the 3 apertures with a=0 and with varying values for a, respectively. Theoretically, the number of intensity levels, N, resulting from n apertures can be expressed as: $N=2^n-1$. For the examples of FIG. 4 and FIG. 5, N=3 and the three aperture shapes produce the seven intensity levels noted above.

Moreover, since each intensity level is a free-floating percentage of the maximum intensity as compared to a fixed percentage of the maximum intensity used in background art IMRT planning tools; the seven intensity levels created by overlapping directly optimized rectangular beam apertures give more flexibility to the treatment planning system in creating optimal treatment plans.

For example, with background art IMRT treatment planning techniques, an intensity pattern containing seven intensity levels of the present invent would require 15 to 30 MLC-shaped apertures to realize, resulting in very inefficient treatment delivery. Although there are only 3 rectangular apertures used in FIGS. 4 and 5 to illustrate the power of the new technique of the invention, the number of apertures, N, at each beam angle would most likely be at least 7 for real treatment plans based on our initial experience. However, the actual number of intensity levels created by these apertures would depend on the planning complexity. Although the number of intensity levels may not reach $2^n-1$, the number would be far beyond that required for acceptable IMRT plans.

For each collimator angle α, a reasonable number (e.g., 7–20) of rectangular beam apertures is set to circumscribe the BEV of the target tumor with sufficient margins. At the start of the optimization, all rectangular beam apertures in the same beam direction are set to have different collimator angles covering a range of collimator angles from 0 to 89 degrees.

The beam apertures are then optimized by an optimization algorithm. The optimization process generally involves three steps. Step (1) of the process is making a modification of a beam aperture by either modifying the position of one of the four sides of the beam aperture by re-positioning the leaves 31, 32, 33, 34 of the independent collimator jaws (FIG. 3), or changing the weighting of the beam aperture (FIG. 4) or changing the orientation of the aperture (FIG. 5). Step (2) of the process is determining if the modification violates the delivery constraints. If the modification violates any of the delivery constraints, the modification will be rejected and a new modification will be randomly determined. If the modification does not violate the delivery constraints, the process proceeds to Step (3). Step (3) is calculating the effects of the modification on dose distribution and, based on the results of the calculation, accepting or rejecting the modifications based on predetermined rules of the optimization. For each modification, a new dose distribution is computed based upon the modified aperture shapes or weights. A non-limiting example of predetermined rules for optimization is simulated annealing lends itself well to the optimization method. However, other optimization techniques may also be used.

Figure 6:
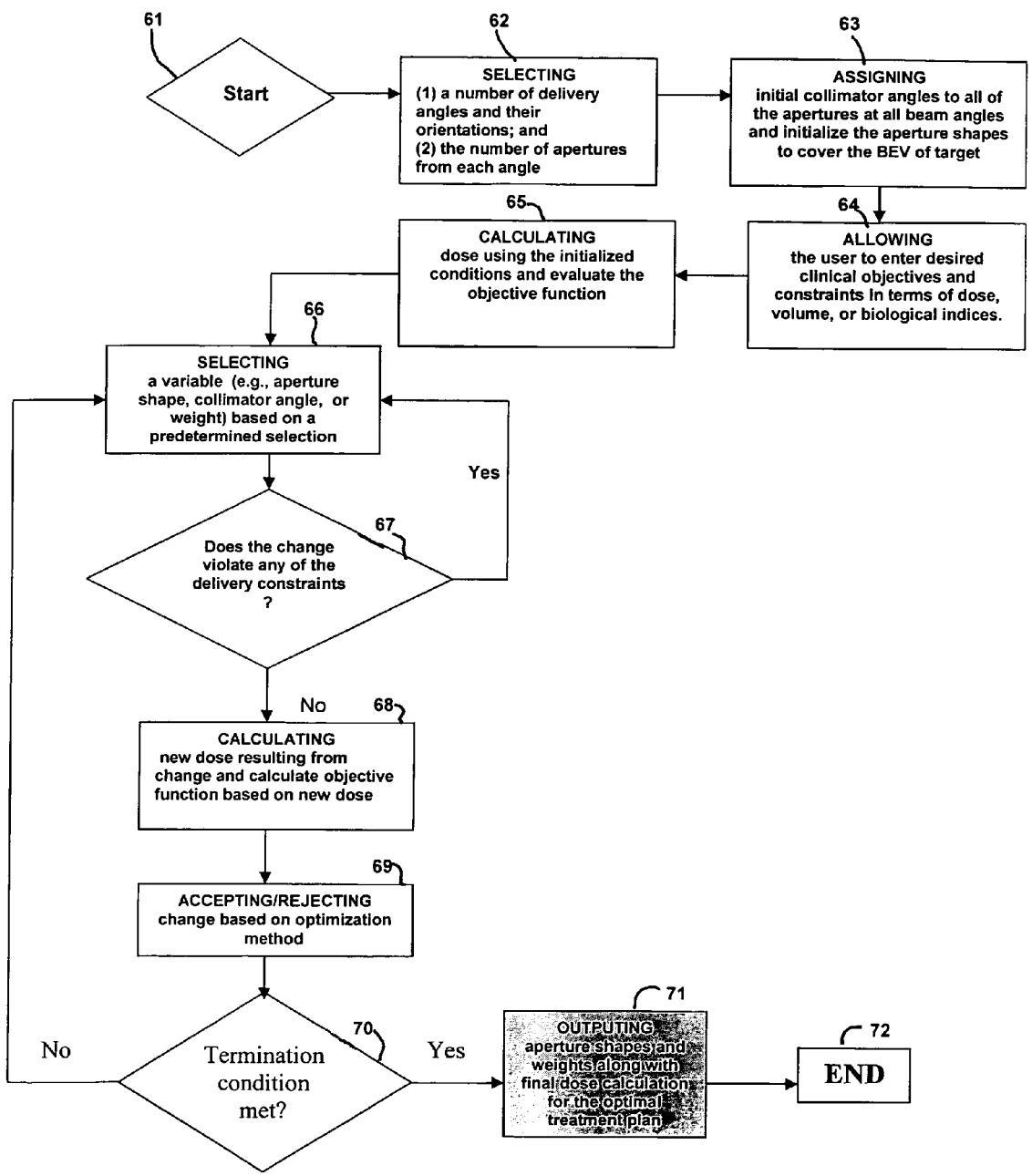
FIG. 6 illustrates the flow diagram of the IMRT technique of the present invention.

FIG. 6 shows a flow chart of the optimization procedure of the present invention. In step 62, the user is selecting a number of beam angles, to be realized during delivery by a combination of rotations of the gantry (FIG. 1, reference 6) and the bed (FIG. 1, reference 16), and the number of rectangular beam apertures assigned to each delivery angle.

After these parameters are entered, the treatment planning computer assigns the initial collimator angles and initial aperture shapes to all of the rectangular beam apertures in a step 63. Any initial collimator angle can be used. One example is for these rectangular beam apertures to be equally distributed within a 90 degree range, which would cover all the possibilities of rectangular shapes. The shapes of the rectangular beam apertures could be initialized such that every aperture circumscribes the BEV of the target tumor. The treatment planning system also assigns a relative intensity (i.e., weight) to each of the aperture shapes. The simplest case is for each of the rectangular beam apertures to start with the same weights.

In step 64, the user defines the clinical objectives of the treatment plan. These objectives are used to score the quality of the treatment plan throughout the optimization process. The quality of the treatment plan can be scored by an objective function that reduces the treatment plan into a single numerical value. The objective function can be of many forms. As a non-limiting example, the objective function can be a least-squares difference between the desired dose and the achieved dose. Alternatively, the objective function can be based on dose volume histograms (DVH) or biological functions.

The optimization process begins in step 65, where the treatment planning computer calculates the radiation dose distribution for the patient using the initial rectangular beam aperture shapes, collimator angles and aperture weights, and evaluates the objective function.

As shown in a step 66, after obtaining an initial score for the quality of the plan, the planning software running on the planning computer selects an optimization variable for further testing. The optimization variables the planning software considers include, but are not limited to, the positions of the collimator jaws used to shape each rectangular aperture for each beam angle, and the relative weight (i.e., intensity) of each aperture shape assigned to each aperture, and the collimator angle of each aperture. A stochastic or deterministic approach can be used to determine the optimization variable for modification and the size of the modification. It is important to note that unlike the background arts, where the weights of the beamlets are modified, resulting in the beam boundaries stair-case shaped, the present invention allows the collimator jaw positions to vary continuously.

Prior to calculating the new dose distribution and objective function resulting from the modification, in a step 67, the planning software determines if one or more geometric constraints is violated by the modification. Some geometric constraints include the collimator jaw positions for the particular LINAC, the granularity of the intensities. If the proposed modified aperture shape or intensity violates any of the constraints, the treatment planning software will reject the modification because the plan containing the proposed modification could not be delivered. The process returns to step 67.

If none of the delivery constraints are violated in step 67, then the planning software calculates the radiation dose applied to the treatment area as a result of the modification in step 68. The dose calculation of a simple rectangular field can be carried out rather quickly and accurately. The value of the objective function is calculated from the new dose distribution and compared with that of the previous modification. If the value of the objective function changed in the desired direction, the software will accept the proposed modification.

If the value of the objective function changed in the undesirable direction, the software either accept or reject the proposed modification of the aperture shape based on some pre-set rules and returns to step 69 for seeking another acceptable modification.

In a preferred embodiment of the present invention, a simulated annealing algorithm is used in step 66 through 70 to determine the optimal aperture shapes, orientations, and aperture weights. The optimization algorithm randomly selects a variable from the set of variables considered in the optimization (i.e., the jaw positions, collimator angles and the weights) of the apertures. For the selected variable, a change of random size is sampled from a probability distribution. For example, a Gaussian distribution could be used. In addition, the shape of the curve could change with successive iterations of the procedure. For example, the width of the Gaussian plot could decrease according to:

$$\sigma = 1 + (A-1)e^{-\frac{\log(n_{succ}+1)}{T_0^{step}}}, \quad (1)$$

where A is the initial Gaussian width, $n_{succ}$ is the number of successful iterations, and $T_0^{step}$ quantifies the rate of cooling.

Although the above formula for the decreasing the magnitude of modification is specific, any scheduled decrease can be used. For example, the step size could be constant throughout the optimization. The goal of the present invention is to achieve the optimal aperture shape for each beam angle as quickly as possible. Decreasing the amplitude of change as the optimization progresses allows coarse samples in the beginning and fine-tuning at the end of the optimization process. In addition, other types of optimization algorithms can be used with the present invention such as conjugate gradient or genetic algorithms.

In step 70, a test is performed to determine whether the optimization process should be terminated. If the optimization process is incomplete, the answer to termination is "NO" and the algorithm returns to step 66. If the optimization process is complete, the answer is "YES" and the algorithm outputs the resulting aperture shapes, weights and the final dose calculation for an optimal treatment plan. Based on pre-defined termination criteria that are dictated by the optimization algorithm, the optimization program will cease the optimization process in step 72. The optimization process can also be terminated or temporarily paused by the operator.

The treatment plan with the optimal value of the objective function is deemed the optimal plan. The output of the optimization algorithm is a set of practical and deliverable rectangular beam apertures at different orientations and their weights, which can be transferred to the control system unit 9 (FIG. 1) of a radiation therapy system 2 (FIG. 1) to direct the delivery of the radiation treatment to a patient.

In addition, the method for optimizing radiation therapy shown in FIG. 6 preferably includes modifying the positions of each of the four sides of the apertures and the weights of these apertures; determining if the modification violates the delivery constraints; and at least one of accepting and rejecting such modifications based on the predetermined rules of the optimization methods.

Further, the method for optimizing radiation therapy shown in FIG. 6 preferably includes at least one of setting delivery constraints in the optimization methods so that all the shapes can be delivered by the LINAC; optimizing rectangular aperture size, location, collimator angle, and beam weights simultaneously; using a small number of rectangular beam field apertures to create a number of intensity levels (N) not exceeding $N=2^n-1$, where n is a number of rectangular shaped beam apertures; and positioning the collimator jaws to vary continuously.

Furthermore, the method for optimizing radiation therapy shown in FIG. 6 preferably includes at least one of optimization methods that are at least one of simulated annealing, mixed integer programming, and iterative projection; using different objective functions to quantify at least one of the desirability and goodness of treatment plans; optimizing rectangular radiation beam field apertures at a given beam angle in a fashion that allow large changes of aperture shapes at the beginning of an optimization and fine-tuning of aperture shapes at the end of the optimization.

Moreover, the method for optimizing radiation therapy shown in FIG. 6 preferably includes at least one of shaping of the radiation beam is performed with multiple rectangular fields with different collimator angles; rectangular fields that are shaped with independent collimator jaws; and at least four (4) independent collimator jaws.

The present invention is not limited to the delivery of intensity modulated treatments. It can also be applied to conventional treatments without intensity modulation. When planning treatments without intensity modulation, methods in the background art of planning simply place a single field per beam angle with a field shape of the BEV of the target tumor.

In contrast to the background art, the present invention uses a computer to optimize multiple fields that can be placed at every beam angle and each of these fields can have different collimator angles. Since the edge of these sub-fields can take any orientation, the placement of multiple fields introduces additional degrees of freedom. Moreover, when the radiation fields of all beam angles are optimized together, what is missing from one angle can be made-up from other angles. This concept allows the radiation to optimally target tumors all areas and with all beam orientations. Therefore, the present invention also unifies treatment planning methods used for both conventional and intensity-modulated techniques.

The present invention does not divide the radiation field into finite-sized beamlets. Thus, the location of the collimator jaws can vary continuously and better conform to the target tumor. In this way more realistic radiation field shapes can be achieved a higher radiation dose can be delivered to the target tumor.

Figure 2:
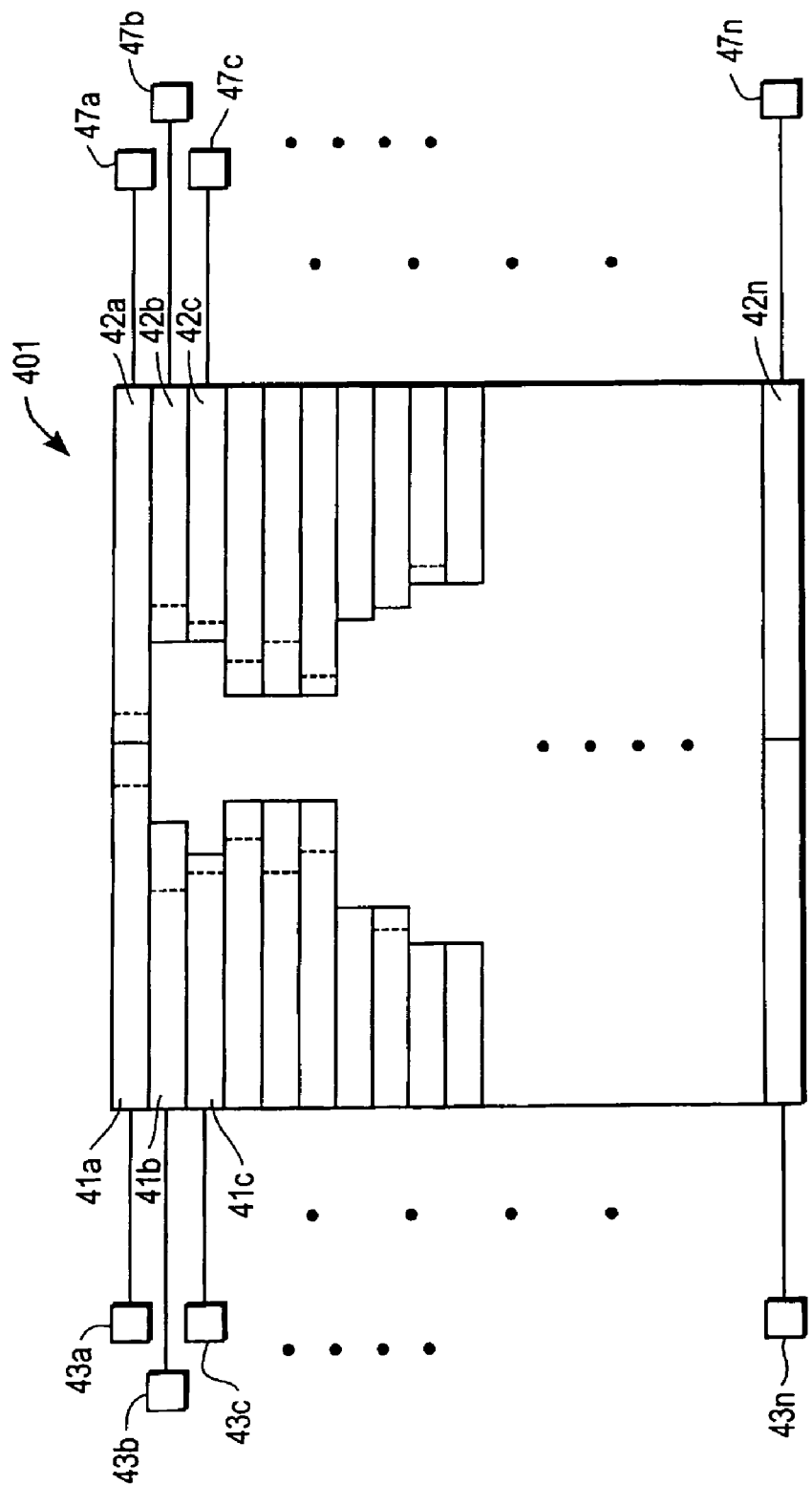
FIG. 2 is an exemplary diagram of a background art multileaf collimator.

Moreover, while IMRT planning of the background art uses the same collimator angle for all radiation field segments, the present invention allows the collimator to change among the radiation field segments. Rather than using a stair-case shaped boundary (FIG. 2) to approximate the actual tumor boundary, the present invention uses multiple segments of straight lines to approximate the tumor boundary. Thus, the present invention provides better conformity to the actual tumor boundary.

The present invention optimizes the positioning of simple independent collimator jaws, thus optimizing the size and location of the rectangular shapes, the collimator angles, and their corresponding intensities based on the treatment goals for a specific patient. As with all treatment planning systems, in order for it to plan the treatment using a specific LINAC, the characteristics of the LINAC including the characteristics of the radiation it generates and the geometric characteristics, such as the geometric limits of all motion, must be entered into the system.

The foregoing description illustrates and describes the present invention. Additionally, the disclosure shows and describes only the preferred embodiments of the invention, but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form or application disclosed herein. Also, it is intended that the appended claims be construed to include alternative embodiments.

I, the Inventor, claim:

1. A method for optimizing radiation therapy that directly optimizes deliverable rectangular fields that overlap at each beam angle and creates intensity modulations for radiation treatment systems, said method comprising:

positioning independent collimator jaws located inside a treatment head of a linear accelerator (LINAC), wherein each jaw can move independently of one another, and
wherein the positioning further comprises:
selecting a plurality of delivery angles, wherein each of the delivery angles has at least one aperture;
assigning collimator angles to each aperture;
assigning weights to each aperture;
assigning aperture shapes for each of the plurality of delivery angles;
defining geometric constraints for a delivery mode and the LINAC;
selecting clinical objectives;
calculating a dose contribution of each of a plurality of discrete pencil beams, wherein the plurality of discrete pencil beams are delivered at the plurality of delivery angles;
calculating a dose distribution and calculating a numeric value of an objective function from the clinical objectives for each of the plurality of delivery angles;
altering at least one of the collimator angles, aperture shapes and weights based on a predetermined selection procedure when any of the geometric constraints for the delivery mode are violated;
calculating the dose distribution resulting from altering at least one of the collimator angles, aperture shapes and weights based on the predetermined selection procedure;
determining whether the geometric constraints for delivery are met;
calculating the objective function based on the dose distribution;
determining whether to one of accept or reject a change in parameters based on at least one optimization method; and
outputting resulting aperture shapes, weights and dose distribution for optimized radiation therapy when the change in parameters is accepted.

2. The method of claim 1, further comprising:
modifying the positions of each of four sides of the apertures and the weights of these apertures;
determining if the modification violates the delivery constraints; and
one of accepting or rejecting such modifications based on the predetermined rules of the at least one optimization method.

3. The method of claim 1, further comprising setting delivery constraints in the at least one optimization method so that all the shapes can be delivered by the LINAC.

4. The method of claim 1, further comprising optimizing rectangular aperture size, location, collimator angles, and beam weights simultaneously.

5. The method of claim 1, further comprising using a small number of rectangular beam field apertures to create a number of intensity levels (N) not exceeding $N=2^{n-1}$, where n is a number of rectangular shaped beam apertures.

6. The method of claim 1, further comprising positioning collimator jaws to vary continuously.

7. The method of claim 1, wherein the at least one optimization method are at least one of simulated annealing, mixed integer programming, and iterative projection.

8. The method of claim 1, further comprising using different objective functions to quantify at least one of the desirability and goodness of treatment plans.

9. The method of claim 1, further comprising optimizing rectangular radiation beam field apertures at a given beam angle in a fashion that allow large changes of aperture shapes at the beginning of an optimization and fine-tuning of aperture shapes at the end of the optimization.

10. The method of claim 1, wherein shaping of the radiation beam is performed with multiple rectangular fields with different collimator angles.

11. The method of claim 1, wherein the rectangular fields are shaped with independent collimator jaws and wherein the collimator angles are altered based on a predetermined selection procedure when any of the geometric constraints for the delivery mode are violated.

12. The method of claim 5, wherein N is at least seven (7).

13. The method of claim 11, wherein there are four (4) independent collimator jaws.

14. The method of claim 1, wherein the collimator angles are altered based on a predetermined selection procedure when any of the geometric constraints for the delivery mode are violated.

* * * * *